(12) United States Patent
Boger et al.

(10) Patent No.: US 7,683,217 B2
(45) Date of Patent: Mar. 23, 2010

(54) PROCESS FOR PREPARING MONOMETHYLHYDRAZINE

(75) Inventors: Uwe Boger, Leverkusen (DE); Ulrich Notheis, Dormagen (DE); Mathias Siekmann, Cologne (DE)

(73) Assignee: Saltigo GmbH, Langenfeld (DE)

( * ) Notice: Subject to any disclaimer, the term of this patent is extended or adjusted under 35 U.S.C. 154(b) by 0 days.

(21) Appl. No.: 12/233,010

(22) Filed: Sep. 18, 2008

(65) Prior Publication Data
US 2009/0187045 A1     Jul. 23, 2009

(30) Foreign Application Priority Data
Sep. 28, 2007   (DE) ................ 10 2007 046 467

(51) Int. Cl.
*C07C 241/02* (2006.01)
(52) U.S. Cl. ...................... 564/464; 564/466
(58) Field of Classification Search ............... 564/464, 564/466
See application file for complete search history.

(56) References Cited

U.S. PATENT DOCUMENTS

| | | | |
|---|---|---|---|
| 2,954,283 A | 9/1960 | Horvitz | |
| 3,423,464 A * | 1/1969 | Bailey | 564/466 |
| 4,281,198 A | 7/1981 | Hojo et al. | |
| 4,855,501 A | 8/1989 | Hojo et al. | |

FOREIGN PATENT DOCUMENTS

| | | |
|---|---|---|
| FR | 1260474 | 6/1960 |
| JP | 58157751 | 9/1983 |
| JP | 60237059 | 11/1985 |

OTHER PUBLICATIONS

Database WPI Week 198343; Thomson Scientific, London, GB; AN 1983-798677 XP002512438. (1983).
Richard L. Hinman: "Base Strengths of Some Alkylhydrazines"; Journal of Organic Chemistry, Bd. 23, 1958, pp. 1587-1588, XP002512432.

* cited by examiner

*Primary Examiner*—Brian J Davis
(74) *Attorney, Agent, or Firm*—Michael A. Miller

(57) ABSTRACT

The present invention relates to a process for preparing monomethylhydrazine by methylating hydrazine or hydrazinium hydrochloride or hydrazinium dihydrochloride with methyl chloride and/or a methano/HCl mixture, characterized in that the reaction mixture formed in the methylation is reacted with an organic base from the group of the alkylamines or alkanolamines and monomethylhydrazine is removed by distillation from the reaction mixture in a low boiler fraction and the low boiler fraction is optionally subjected to a further distillation.

7 Claims, No Drawings

PROCESS FOR PREPARING MONOMETHYLHYDRAZINE

The present invention relates to a process for preparing monomethylhydrazine.

Monomethylhydrazine, referred to hereinafter as MMH, is a valuable starting material for the preparation of crop protection agents and pharmaceuticals. However, it is also used as a fuel in aerospace and rocket technology.

On the industrial scale, MMH is prepared predominantly by a modified Raschig process. In a first step, chloranine is prepared from ammonia and sodium hypochlorite, and is then reacted in a second step with methylamine to give MMH.

Alternatively, methylurea can be reacted with sodium hydroxide and sodium hypochlorite to give MMH. The two processes lead to a very low product concentration, such that energy-intensive separation steps with complicated plants are required for the concentration and purification.

Additionally known is a process for nitrosating methylamine and hydrogenating the nitrosamine formed to give methylbydrazine. Owing to the carcinogenicity of the intermediate, the process, however, is not employed industrially.

In addition, MMH can be prepared by alkylating hydrazine or hydrazine compounds. In this field, various processes have been described.

Industrially available alkylating agents which have been described include, for example, dimethyl sulfate, methyl chloride, methanol/methyl chloride, methanol in the presence of an HCl source, and trimethylanilinium halides.

Generally, in the alkylation of hydrazine, there is the difficulty that the reaction does not stop at the stage of monoalkylation, and instead, according to the reaction conditions and degree of alkylation, mixtures of unconverted hydrazine, MMH, and polyalkylated hydrazines such as symmetrical dimethylhydrazine (SDMH), unsymmetrical dimethylhydrazine (UDMH) and trimethylhydrazine (TMH) and hydrazinium compounds are obtained, which may be difficult to separate.

When the hydrazine compound alkylated is not the free hydrazine but rather a hydrazinium salt, higher temperatures are required, but the selectivity for the monoalkylated product at the same conversion is higher than in the case of alkylation of the free hydrazine.

Typically, therefore, only a partial conversion based on hydrazine or hydrazine compound is established in order to achieve a high selectivity for the monoalkylated product. For the economic viability, it is then particularly important to efficiently remove and to recycle unconverted hydrazine.

After the alkylation, the leaving group of the alkylating agent—optionally with release of a further uncharged molecule—forms a salt in the reaction mixture with the hydrazines. The alkylhydrazines formed and/or the starting hydrazine have to be released from this salt in the workup and removed.

MMH and hydrazine form binary high boiler azeotropes with water. The MMH/water azeotrope contains approx. 3 mol of water for 1 mol of MMH and boils at 102-106° C. Hydrazine forms an equimolar azeotrope with water, which boils at 120-121° C. If the intention, therefore, is to remove the hydrazines from the newly formed salt after their release with alkali metal hydroxide, according to the composition, first water, then the MMH/water azeotrope, then the hydrazine/water azeotrope are distilled over, and the salt remains as a solid. In industry, this requires specialized complicated apparatus. Moreover, in solids-containing mixtures, there is the risk of crust formation and of local overheating, which has to be avoided for reasons of the thermal stability of hydrazine.

U.S. Pat. No. 2,954,283 describes the preparation of a mixture predominantly composed of MMH and UDMH by reacting dimethyl sulphate with hydrazine or hydrazinium sulphate. Dimethyl sulphate as an alkylating agent has the disadvantage that the two methyl groups cannot be exploited fully. The methylsulphuric acid formed in the case of incomplete exploitation has very poor biodegradability and therefore has to be hydrolysed in an additional step.

DE-A 31 48 971 describes a process for preparing monomethylhydrazine, in which hydrazine hydrochloride is reacted with methanol in the presence of hydrazine dihydrochloride or methyl chloride to give monomethylhydrazine hydrochloride. Conversions of hydrazine monohydrochloride of no more than 30% are described. The product mixture is then freed of methanol and methyl chloride by distillation, which can be recycled. Any water present is likewise removed by distillation. Methanol is then added to the residue, which precipitates crystalline hydrazine monohydrochloride as a solid which is removed. This hydrazine hydrochloride can be recycled into the reaction. The mixture remaining after the removal of hydrazine hydrochloride is admixed with aqueous alkali solution. This releases the methyl hydrazine which can be isolated and purified by distillation.

However, this process has the disadvantage that good selectivities for MMH are achieved only in the case of relatively low conversions, as shown by in-house experiments.

Moreover, the process requires the distillative removal of methanol and water from the reaction mixture and then the addition of fresh methanol.

Hydrazine hydrochloride is partly soluble in methanol, such that, after neutralization of the mother liquor with sodium hydroxide solution, both monomethylhydrazine and hydrazine get into the rectification step. The hydrazine likewise has to be removed here and recycled. The rectification step described additionally has the serious disadvantage that, after the distillation of the hydrazines released, a solid residue of NaCl remains in the bottom. This distillation can therefore be done only in specific apparatus and is also critical for safety reasons in view of the decomposition tendency of the hydrazines.

Without recycling of the hydrazine hydrochloride, the process is uneconomic owing to the low yield based on hydrazine used. Therefore, large amounts of unconverted hydrazine hydrochloride have to be recycled again in a complicated workup with handling of solids.

JP-A-58157751 describes an alternative process for obtaining monomethylhydrazine from monomethylhydrazine hydrochloride-containing product mixtures which have been prepared by reacting hydrazine hydrochloride with methanol in the presence of hydrazine dihydrochloride or methyl chloride.

In this case, the reaction mixture is concentrated by distillative removal of methanol and water and admixed with a 1.2- to 2-fold excess of hydrazine hydrate (HyHy) based on hydrochloride present. This mixture, which contains 2.2-3.0 mol of hydrazines based on hydrochloride present, is then distilled in order to release the methylhydrazine which has a lower boiling point than hydrazine. A portion of the hydrazine added can also be recovered. The maximum temperature of the reaction mixture in the distillation should be below 120° C., which requires a vacuum distillation given a boiling point of hydrazine hydrate of 120° C.

However, leaks in the apparatus, which can lead to ingress of air and reaction of the hydrazines with atmospheric oxygen, must be ruled out, which necessitates extensive safety measures for an industrial plant.

The method described is therefore disadvantageous as an industrial process.

JP-A-60237059 describes a process for preparing monoalkylhydrazines, in which hydrazine, methanol and a hydrohalic acid are reacted in the presence of a phosphorus-containing oxygen acid to give monomethylhydrazine. The reaction mixture is concentrated under reduced pressure and neutralized with 50% sodium hydroxide solution. An inorganic solid precipitates out. This solid is removed by filtration and washed once again, and the combined liquid phases are fractionally distilled. After the distillation, an inorganic salt remains, which comprises large parts of the unconverted hydrazine. Recycling of the hydrazine is not described.

Owing to the low yield based on hydrazine used, the process is uneconomic.

DE-A 30 26 771 describes a process for preparing MMH and unsymmetrical dimethylhydrazine (UDMH), characterized in that trimethylanilinium halide is reacted with hydrazine or MMH. An excess of 5 to 12:1 of hydrazines to trimethylanilinium halide is used. Dimethylaniline formed is removed by phase separation as the organic phase, and MMH and UDMH are obtained by distilling the aqueous phase.

This process has the disadvantage that dimethylaniline has to be recycled and reacted in an additional step with methyl chloride to give the alkylating agent.

It is thus an object of the present invention to provide a process for preparing monomethylhydrazine, which can be performed in conventional multipurpose apparatus without complicated development from readily available chemicals.

The invention relates to a process for preparing methylhydrazine, characterized in that 1) alkylation of hydrazine or hydrazinium hydrochloride with methyl chloride, methanol and HCl, methanol and hydrazinium dihydrochloride or mixtures thereof forms a crude product which comprises hydrazine, monomethylhydrazine, dimethylhydrazines and/or trimethylhydrazine, and also water and HCl, 2) the hydrazines in this mixture are released with a molar excess of an organic base, based on the hydrochlorides present in the crude product, and 3) are removed by distillation from the hydrochloride of the organic base remaining in the bottoms.

The invention therefore provides a process for preparing monomethylhydrazine from the methylation of hydrazine or hydrazinium hydrochloride or hydrazinium dihydrochloride with methyl chloride and or a methanol/HCl mixture, characterized in that the reaction mixture formed in the methylation is reacted with an organic base at a pKa greater than 7.0 and a boiling point above 120° C., and monomethylhydrazine is removed by distillation from the reaction mixture in a low boiler fraction and the low boiler fraction is optionally subjected to a further distillation.

According to the invention, the reaction mixture can be obtained by various routes.

Firstly, the reaction mixture can be prepared by reacting hydrazine hydrochloride with methanol in the presence of an excess of HCl (based on hydrazine), as described, for instance, in DE-A 3148971. The HCl excess can be generated by adding hydrazine dihydrochloride, HCl or methyl chloride. Without the excess, the reaction does not proceed. Preference is given to establishing a 5-20% HCl excess.

In one procedure, hydrazine hydrate can be initially charged in a reactor and gaseous HCl can be metered in. HCl can also be added in the form of aqueous hydrochloric acid.

Preference is given to the addition of HCl as a gas. The amount of water based on hydrazine is 1:1 (HyHy with gaseous HCl) to about 10:1 (relatively dilute hydrazine solution with aqueous HCl). Preference is given to water contents of 1:1 to 5.5:1, more preferably 1:1 to 3:1.

According to the invention, the reaction takes place at temperatures of 90 to 150° C., preferably 100 to 130° C. The pressure in the reaction depends on the reaction temperature, the amounts of methanol and water and the amount of excess HCl.

A pressure of 2 to 15 bar, particularly of 2 to 5 bar, is typically preferred.

In a further embodiment, hydrazine hydrochloride is initially charged with the excess of HCl and brought to temperature. Methanol is then metered in until the desired pressure has been attained, and the rate of metered addition of methanol is adjusted such that the pressure in the system remains constant. After the metered addition has ended, the pressure falls and the time at which it does not change any further is awaited.

The molar amount of methanol may be between 50% and 600% based on hydrazine and can be converted completely or only partly. The higher the amount of methanol converted, the lower the selectivity for MMH. However, the yield rises further up to a ratio of about 1:1. Preference is given to selecting the amount of methanol and the duration of the reaction such that, at the end of the reaction, all methanol added has reacted. In this case, amounts of methanol of 0.5:1 to 1:1 based on hydrazine are preferred.

Secondly, the reaction mixture can be obtained by reacting hydrazine with methyl chloride. Hydrazine can be used in the form of a hydrazine hydrate or in the form of a more dilute aqueous solution. Preference is given to the use of 100% hydrazine hydrate.

Methyl chloride can be used in the form of a gas or in compressed form as a liquid under appropriate pressure. The reaction can be conducted batchwise with metered addition of methyl chloride or continuously.

The reaction temperatures are between 40 and 100° C., preferably between 60 and 90° C. The pressure depends on the amount of methyl chloride and the reaction temperature. Predetermining the temperature and the amount of methyl chloride or the rate of metered addition of the methyl chloride allows the pressure to be adjusted to the requirements of the apparatus selected. It is typically in the range between 1 and 10 bar, preferably between 1 and 6 bar.

Since the selectivity for MMH depends greatly on the conversion in this embodiment, it is advantageous to restrict the conversion based on hydrazine to 50%, preferably 30%.

The reaction mixtures thus prepared are processed further as follows:

Should the reaction mixture still contain volatile compounds such as methanol or methyl chloride, they are removed by distillation before the hydrazines are released.

The above-described reaction mixture is reacted with an organic base in a ratio of 1:1.05 to 1:3, preferably 1:1.05 to 1:2, more preferably 1:1.05 to 1:1.3. Volatile components which are removed at least partly via the top in the inventive distillation are hydrazine, MMH, UDMH, SDMH, TMH and water.

Organic bases used in the process according to the invention have the following features:

Their pKa value greater than 7.0 is above that of hydrazine, preferably above pKa=8.0, more preferably above pKa=9.0.

Its standard boiling point is above the boiling point of the hydrazine/water azeotrope, i.e. above 120° C. but below 250° C., preferably above 140° C. and below 220° C. at ambient pressure, more preferably between 160° C. and 200° C. at ambient pressure.

They do not form azeotropes with water which boil below the MMH/water azeotrope; more preferably, they do not form any azeotropes with water.

Their hydrochlorides are liquid under distillation conditions.

Examples of bases suitable in accordance with the invention are monoethanolamine, diethanolamine and triethanolamine or mixtures thereof. Preference is given to monoethanolamine, diethanolamine and mixtures as obtained in the industrial synthesis of these compounds. Particular preference is given to monoethanolamine and diethanolamine. Very particular preference is given to monoethanolamine.

The amounts of organic base which are also distilled via the top depend, in a manner known per se, on the separating performance of the column used and the reflux ratio established. Preference is given to using a column with 1-20 theoretical plates and to establishing a reflux ratio of 0.1:1 to 10:1. The better the retention of the organic base in the bottom, the smaller the excess of organic base which can be selected.

The distillation can in principle be conducted batchwise, semibatchwise or continuously. Preference is given to semibatchwise or continuous methods. The distillation can be conducted at ambient pressure or under reduced pressure. Preference is given to distillation at standard pressure.

In a preferred semibatchwise embodiment, the organic base is initially charged and brought to a temperature between 130° C. and the boiling point of the base, preferably 130-170° C., and the methanol-free reaction mixture is metered into the base in such a way that methylhydrazine is distilled off completely via the top. The hydrochloride of the base and the base remain in the bottoms. During the distillation, hydrazine decomposes partly. The composition of the top product can be controlled via the top temperature and influenced via the reflux ratio. The top temperature at ambient pressure is between 100° C. and the boiling point of the base, preferably between 100° C. and 130° C. The rate of metered addition is established such that there is no safety-critical enrichment of hydrazines in the bottoms.

In another preferred semibatchwise embodiment, the reaction mixture is metered in such that all volatile components are distilled off directly via the top.

In a preferred continuous embodiment, the reaction mixture is mixed with the organic base and then evaporated continuously in a suitable apparatus. Suitable apparatus includes apparatus for a continuous distillation, for example thin-film evaporators, short-path evaporators or falling-film evaporators. The temperature and residence time in the evaporator are adjusted such that MMH is distilled off completely via the top. The evaporator can be operated in conjunction with a separating column (for example column with structured packing or random packing or tray column).

Optionally, a portion of the organic base can be replaced by an alkali metal hydroxide, preferably NaOH or aqueous sodium hydroxide solution, such that the bottoms of the distillation still remain conveyable in the effluent.

When the volatile compounds are removed, the remaining amounts of free organic base are removed from the bottoms and recycled. This thermally decomposes the last traces of hydrazines present in the bottoms.

When the organic base is an alkanolamine such as monoethanolamine, the bottoms which then remain contain only readily biodegradable organic components and can—optionally after neutralization with a base such as sodium hydroxide solution or milk of lime—be disposed of as wastewater in a water treatment plant.

When the organic phase, after release with a strong aqueous inorganic base, forms a second liquid phase as well as the aqueous salt solution, this can be removed and recycled again.

Optionally, the resulting low boiler fraction which comprises MMH can be sent to a further distillation (fine distillation) for removal of UDMH, SDMH and any further by-products.

In a particularly preferred embodiment, 100% hydrazine hydrate is reacted continuously with methyl chloride in a tubular reactor or a tank battery having up to four tanks. The reaction mixture is reacted with the organic base and the volatile components are removed continuously via the top. The alkylhydrazines MMH and UDMH removed via the top are removed in a second distillation step from the hydrazine hydrate, which is recycled back into the reaction. Subsequently, the mixture of UDMH and MMH is distilled further in a known manner to give saleable MMH and UDMH. The fine distillation can be carried out continuously or else batchwise.

EXAMPLES

General

The hydrazine analyses were carried out by means of capillary electrophoresis.

Comparative Example 1 (Noninventive)

Semibatchwise Distillation with tri-n-propylamine (NPr$_3$) as the Base

A 2 l four-neck flask with mechanical stirrer and an attached silver-jacketed column of length 20 cm and diameter 25 mm, which was filled with 4×4 mm Raschig rings and provided with an automatic reflux divider, was initially charged with 525 g (3.6 mol) of tripropylamine and heated to 160° C. Within 1 hour and 35 minutes, a peristaltic pump was used to pump 200 g of an aqueous reaction mixture which contained 19 g of hydrazine, 32 g of MMH, 22 g of polyalkylated hydrazines and 66 g of HCl into the boiling tripropylamine. 10 minutes after the start of metered addition, the reflux divider was switched from complete reflux to a reflux ratio R:E of 4:1. Within 3 hours, 172 g of a mixture which contained only 2 g of MMH distilled over (distillation yield 6%).

Comparative Example 2 (Noninventive)

Semibatchwise Distillation with N-methylimidazole as the Base

The procedure is as in Comparative Example 1, except that the amine initially charged was 470 g of N-methylimidazole which was heated to 170° C. Within 1 hour and 33 minutes, a peristaltic pump was used to pump 308 g of an aqueous reaction mixture which contained 29 g of hydrazine, 50 g of MMH, 35 g of polyalkylated hydrazines and 99 g of HCl into the boiling N-methylimidazole. 14 minutes after the start of metered addition, the reflux divider was switched from complete reflux to a reflux ratio R:E of 4:1. Within 4 hours and 15 minutes, 142 g of a mixture which contained only 2.4 g of MMH distilled over (distillation yield 5%).

Example 1

Preparation of a Crude Mixture from Hydrazine Hydrochloride and Methanol

In a water bath, a solution of 1269 g of hydrazine hydrochloride, 102 g of hydrazine dihydrochloride and 349 g of water was prepared and transferred to a 3 l steel-enamel autoclave with a stirrer and immersed tube. The autoclave was closed and heated to 130° C. Within 4 hours, 560 g of methanol were pumped in at 110° C. such that the pressure did not exceed 4 bar. Subsequently, stirring was continued for 4 hours, and the autoclave was cooled to 60° C., decompressed and emptied. The product contained 9.8% by weight of hydrazine, 16.9% by weight of MMH, 5.0% by weight of UDMH, 4.4% by weight of SDMH and 1.8% by weight of TMH, and also 32.8% by weight of HCl.

Example 2

Semibatchwise Distillation with Monoethanolamine (MEA) as the Base

A 2 l four-neck flask with a mechanical stirrer and an attached silver-jacketed column of length 40 cm and diameter 25 mm, which had been filled with 4×4 mm Raschig rings and provided with an automatic reflux divider, was initially charged with 605 g (9.8 mol) of monoethanolamine and heated to 170° C.

Within 2 hours and 33 minutes, 800 g of the solution prepared in Example 1 were pumped in. The top temperature was between 103 and 107° C., the bottom temperature 150° C. The reflux ratio was 4:1. After the end of metered addition, distillation was continued under the same conditions for 2 hours and 10 minutes. A fraction of 496 g was withdrawn, which contained 26.5% by weight of MMH (corresponding to 97% of the MMH used in the distillation) and 0.4% ethanolamine.

Subsequently, distillation was continued initially at ambient pressure and a bottom temperature of 170° C., then vacuum was applied slowly and a second fraction of 208 g was distilled off under reduced pressure up to a bottom temperature of 200° C. and top pressure 10 mbar, which contained 75.2% by weight of ethanolamine, 11.5% by weight of hydrazine and 1.5% by weight of MMH, and which was usable in the next distillation.

Example 3

Preparation of a Crude Mixture of Hydrazine and Methyl Chloride

A 1.4 l enamel autoclave was initially charged with 400 g (8 mol) of hydrazine hydrate and the autoclave was heated to 80° C. At this temperature, 101 g (2 mol) of methyl chloride were metered in within 3 hours and 15 minutes at such a rate that the pressure did not exceed 4 bar. After the end of metered addition, stirring was continued for 3 hours, the mixture was cooled to room temperature and decompressed, and the product was withdrawn. The product contained 42.0% by weight of hydrazine, 8.9% by weight of methylhydrazine, 4.8% by weight of UDMH and 12.5% by weight of chloride.

Example 4

Distillation of a Crude Mixture Using a Thin-Film Evaporator at 140° C.

178.8 g of the reaction product prepared in Example 3, which contained 0.63 mol of chloride, were admixed with 46.2 g (0.76 mol) of monoethanolamine and introduced into a receiver heated to 90° C. From this receiver, the mixture was conducted within 1 hour and 5 minutes through a Sambay laboratory thin-layer evaporator having a heating area of 155 cm². The heating medium temperature was 140° C. 83 g of distillate and 142 g of bottom product were obtained. The distillate contained 16.7% by weight of MMH (corresponding to 82% of the MMH used in the distillation).

Example 5

Distillation of a Crude Mixture Using a Thin-Film Evaporator at 150° C.

287 g of the reaction product prepared in Example 3, which contained 1.01 mol of chloride, were admixed with 74 g (1.21 mol) of monoethanolamine and introduced into a receiver heated to 90° C. From this receiver, the mixture was conducted within 1 hour and 41 minutes through the Sambay laboratory thin-layer evaporator from Example 4. The heating medium temperature was 150° C. 185 g of distillate and 176 g of bottom product were obtained. The distillate contained 13.5% by weight of MMH (corresponding to 98% of the MMH used in the distillation).

Example 6

Distillation of a Mixture with a Thin-Layer Evaporator at 160° C.

243 g of the reaction product prepared in Example 3, which contained 0.86 mol of chloride, were admixed with 62.7 g (1.03 mol) of monoethanolamine and introduced into a receiver heated to 90° C. From this receiver, the mixture was conducted within 2 hours and 55 minutes through the Sambay laboratory thin-layer evaporator from Example 4. 181 g of distillate and 125 g of bottom product were obtained. The distillate contained 11.8% by weight of NMH (corresponding to 99% of the MMH used in the distillation).

The invention claimed is:

1. Process for preparing monomethlyhydrazine from the methylation of hydrazine or hydrazinium hydrochloride or hydrazinium dihydrochloride with methyl chloride and/or a methanol/HCl mixture, characterized in that the reaction mixture formed in the methylation is reacted with an organic base at a pKa greater than 7.0 and a boiling point above 120° C., and monomethylhydrazine is removed by distillation from the reaction mixture in a low boiler fraction and this low boiler fraction is optionally subjected to a further distillation.

2. Process according to claim 1, characterized in that the reaction mixture is reacted with the organic base in a ratio of 1:1.05 to 1:3, based on the reaction mixture.

3. The process according to claim 1, characterized in that a portion of the organic base is replaced by alkali metal hydroxide.

4. The process according to claim 1, characterized in that the organic base is triethanolamine, diethanolamine, monoethanolamine or a mixture thereof.

5. The process according to claim 1, characterized in that the low boiler fraction is removed by distillation by means of a column having 1 to 20 theoretical plates at a ref lux ratio of 0.1:1 to 10:1.

6. The process according to claim 1, characterized in that the low boiler fraction is separated by distillation into a fraction comprising monomethylhydrazine (MMH) and a fraction comprising the remaining by-products.

7. The process according to claim 1, characterized in that the reaction mixture is reacted with the organic base at a temperature in the range of 130 to 170° C.

* * * * *